(12) United States Patent
Hubbs et al.

(10) Patent No.: US 6,552,217 B2
(45) Date of Patent: Apr. 22, 2003

(54) PROCESS FOR THE PREPARATION OF ALKYL 1-METHYLCYCLOPROPANECARBOXYLATE

(75) Inventors: John Clark Hubbs, Kingsport, TN (US); David Carl Attride, Jonesborough, TN (US); Neil Warren Boaz, Kingsport, TN (US); James Charles Ciula, Kingsport, TN (US); John Thorton Maddox, Jonesborough, TN (US); Thomas Nabih, Kingsport, TN (US); William Dell Nottingham, Kingsport, TN (US); David Chris Spencer, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/897,872

(22) Filed: Jul. 2, 2001

(65) Prior Publication Data

US 2002/0016493 A1 Feb. 7, 2002

Related U.S. Application Data

(60) Provisional application No. 60/222,317, filed on Aug. 1, 2000.

(51) Int. Cl.⁷ ........................ C07C 69/74; C07C 209/00
(52) U.S. Cl. ........................ 560/124; 560/226; 549/295; 549/326; 564/134; 564/142; 564/190; 564/448
(58) Field of Search .................... 560/124, 226; 549/295, 326; 564/134, 142, 190, 448

(56) References Cited

U.S. PATENT DOCUMENTS

| | | | |
|---|---|---|---|
| 3,299,100 A | * 1/1967 | Philipps | 260/343.6 |
| 3,503,971 A | 3/1970 | Neighbors et al. | |
| 3,711,549 A | 1/1973 | Phillips et al. | |
| 4,520,209 A | 5/1985 | Schwarze et al. | |
| 4,590,292 A | * 5/1986 | Blackwell et al. | 560/124 |
| 4,705,788 A | 11/1987 | Schriewer et al. | |
| 4,778,920 A | * 10/1988 | Kaufhold | 560/124 |
| 5,371,270 A | 12/1994 | Kaufhold et al. | |
| 5,504,245 A | * 4/1996 | Liang et al. | 562/506 |
| 5,849,949 A | * 12/1998 | Steffen | 562/483 |

FOREIGN PATENT DOCUMENTS

| | | |
|---|---|---|
| DE | 3026094 | 11/1982 |
| GB | 2008110 A | 5/1979 |
| GP | 2008111 A | 5/1979 |

OTHER PUBLICATIONS

Shuliang Wang et al, Chem. Abst. 121:108017 ["Synthesis of cyclopropylamine", Zhongguo Yiyao Gongye Zazhi, vol. 24 (1993), pp. 514–516].*
Siegel et al., J. Am. Chem. Soc., 1950, vol. 72, pp. 3815–3817.
Cannon et al., J. Am. Chem. Soc., 1959, vol. 81, pp. 1660–1666.
Selva et al., J. Chem. Soc. Perkin Trans. 1; 1994, pp. 1323–1328.
Ishikawa et al., Chem. Pharm. Bull., 1995, vol. 43, No. 11, 2014–2018.

* cited by examiner

Primary Examiner—Paul J. Killos
(74) Attorney, Agent, or Firm—Michael J. Blake; Bernard J. Graves, Jr.

(57) ABSTRACT

Disclosed is a 4-step process for the preparation of alkyl esters of 1-methylcyclopropanecarboxylic acid which comprises the steps of (1) converting γ-butyrolactone to α-methyl-γ-butyrolactone; (2) converting the α-methyl-γ-butyrolactone from step (1) to an alkyl 4-halo-2-methylbutyrate; (3) producing a xylene solution of the alkyl 4-halo-2-methylbutyrate; and (4) contacting the xylene solution of an alkyl 4-halo-2-methylbutyrate from step (3) with an alkali metal alkoxide under conditions of temperature and pressure which causes vaporization of (i) an alkanol as it is formed and (ii) an alkyl 1-methylcyclopropanecarboxylate as it is formed from the alkyl 4-halo-2-methylbutyrate. Also disclosed are processes whereby the alkyl 1-methylcyclopropanecarboxylate, prepared as described above, is converted to 1-methylcyclopropylamine.

10 Claims, No Drawings

PROCESS FOR THE PREPARATION OF ALKYL 1-METHYLCYCLOPROPANECARBOXYLATE

This application claims the benefit of U.S. Provisional Application No. 60/222,317, filed Aug. 1, 2000.

FIELD OF THE INVENTION

This invention pertains to a process for the preparation of alkyl esters of 1-methylcyclopropanecarboxylic acid. More specifically, this invention pertains to a process for the synthesis of alkyl 1-methylcyclopropanecarboxylates by a novel combination of steps starting with γ-butyrolactone.

BACKGROUND OF THE INVENTION

The present invention is directed to an improved process for the production of alkyl esters of 1-methylcyclopropanecarboxylic acid. This method includes the preparation of a solution of an alkyl 4-halo-2-methyl butyrate in a solvent such as xylene with the purification and continuous removal of the alkyl ester of 1-methylcyllopropanecarboxylate as it is formed. The most common method used to form alkyl esters of 1-methylcyclopropane carboxylic acid involves carbene insertion into esters of α-methylacrylic acid. For example, Siegel et. al. (*J. Am. Chem. Soc*, 1950, 72, pages 3815–3817) disclose the reaction of diazomethane with methyl methacrylate to produce methyl 1-methylcyclopropane carboxylate in a 63% yield. The tendency for diazomethane to explode limits its use on an industrial scale.

Cannon and coworkers (*J. Am. Chem. Soc.*, 1959, 81, pages 1660–1666) disclose the reaction of α-methyl-γ-chlorobutyric acid ethyl ester with sodamide under strictly anhydrous conditions in benzene to provide 1-methylcyclopropane carboxylic acid ethyl ester in a yield of 47.6%. Schwarze and coworkers, U.S. Pat. No. 4,520,209, disclose the reaction of methyl 4-chloro-2-methylbutyrate in methanol with an excess of sodium methylate at a reaction temperature of 90° C. or higher. Although, an 87% yield was claimed by Schwarze et al., wiped film distillation or extraction was required to the separate methyl 1-methylcyclopropanecarboxylate from the sodium chloride by-product. Schwarze and coworkers disclose a boiling point for methyl 1-methylcyclopropanecarboxylate of 136° C. German Patent Publication DE 3026094 discloses the conversion of 4-chloro-2-methylbutyrate to 1-methylcyclopropaneamide via sodium methoxide/ammonia in an autoclave at 145° C.

There still exists a need for improved methods for the manufacture of alkyl esters of 1-methylcyclopropanecarboxylic acid. These esters are valuable intermediate products for the production of agrochemicals and pharmaceuticals. In particular alkyl esters of 1-methylcyclopropane carboxylic acid are useful intermediates for the manufacture of 1-methylcyclopropanecarboxamide and 1-methylcyclopropylamine.

BRIEF SUMMARY OF THE INVENTION

The process provided by the present invention for the preparation of alkyl 1-methylcyclopropanecarboxylate comprises the steps of:

(1) contacting γ-butyrolactone with dimethylcarbonate in the presence of a basic catalyst to produce α-methyl-γ-butyrolactone;

(2) contacting the α-methyl-γ-butyrolactone from step (1) with a hydrogen halide in the presence of an alkanol to produce a reaction mixture containing an alkyl 4-halo-2-methylbutyrate;

(3) contacting the reaction mixture of step (2) with xylene to produce a xylene solution of an alkyl 4-halo-2-methylbutyrate;

(4) contacting the xylene solution of an alkyl 4-halo-2-methylbutyrate from step (3) with an alkali metal alkoxide under conditions of temperature and pressure which causes vaporization of (i) an alkanol as it is formed and (ii) an alkyl 1-methylcyclopropanecarboxylate as it is formed from the alkyl 4-halo-2-methylbutyrate.

The alkyl 1-methylcyclopropanecarboxylates obtained from our novel process may be converted to 1-methylcyclopropylamine by the steps of:

(5) contacting the alkyl 1-methylcyclopropanecarboxylate with an alkali metal hydroxide, carbonate or bicarbonate in the presence of water and a lower alkanol, e.g., an alkanol containing up to about 4 carbon atoms to produce an alkali metal 1-methyl cyclopropanecarboxylate;

(6) contacting the alkali metal 1-methylcyclopropanecarboxylate produced in step (5) with an acid to convert the alkali metal 1-methylcyclopropanecarboxylate to 1-methylcyclopropanecarboxylic acid;

(7) contacting the 1-methylcyclopropanecarboxylic acid produced in step (6) with thionyl chloride to convert the 1-methylcyclopropanecarboxylic acid to 1-methylcyclopropanecarbonyl chloride;

(8) contacting the 1-methyl cyclopropanecarbonyl chloride from step (7) with ammonia to convert the 1-methyl cyclopropanecarbonyl chloride to 1-methyl cyclopropanecarboxamide; and (9) contacting the 1-methyl cyclopropanecarboxamide from step (8) with an alkali metal hydroxide and an alkali metal hypochlorite in the presence of water to convert the 1-methyl cyclopropanecarboxamide to 1-methyl cyclopropylamine.

A single-step embodiment of the present invention comprises the process of step (4) wherein an alkyl 1-methylcyclopropanecarboxylate is prepared and recovered by contacting a xylene solution of an alkyl 4-halo-2-methylbutyrate with an alkali metal alkoxide under conditions of temperature and pressure which causes vaporization of (i) an alkanol as it is formed and (ii) an alkyl 1-methylcyclopropanecarboxylate as it is formed from the alkyl 4-halo-2-methylbutyrate. 1-Methylcyclopropylamine is useful in the synthesis of antibacterial compounds described in U.S. Pat. No. 4,705,788.

DETAILED DESCRIPTION

The first step of the process is carried out by contacting γ-butyrolactone with dimethylcarbonate in the presence of a basic catalyst to produce α-methyl-γ-butyrolactone. This reaction is described by M. Selva et al., *J. Chem. Soc. Perkin Trans.* 1; 1994, 1323, although methods for isolation of the product are not disclosed. In this step the dimethylcarbonate functions as both a solvent and reactant (methylating agent). Typically, the amounts of dimethylcarbonate and γ-butyrolactone employed give a dimethylcarbonate:γ-butyrolactone mole ratio in the range of about 1:1 to 20:1, preferably about 5:1 to 20:1. The first step may be carried out at a temperature in the range of about 160 to 250° C., preferably about 200 to 240° C. Especially preferred are reaction temperatures of about 210 to 240° C. and reaction times of about 1 to 14 hours. Longer reaction times and higher temperatures permit the complete conversion of γ-butyrolactone which facilitates distillative purification of the produced α-methyl-γ-butyrolactone. The reaction of γ-butyrolactone with dimethylcarbonate normally is carried out under super-atmospheric pressure, e.g., pressures in the range of about 27 to 90 bars absolute (bara—about 400 to 1300 pounds per square inch—psi). The basic catalyst employed in the first step may be selected from the alkali metal hydroxides, carbonate and bicarbonates, preferably the hydroxides and carbonates of sodium and potassium. Because of its solubility in the reaction mixture, potassium carbonate is the most preferred basic catalyst. The amount of basic catalyst used may be in the range of about 0.1 to 2 mole equivalents, preferably 0.5 to 2 mole equivalents, per mole of γ-butyrolactone reactant. Careful distillation will provide a product stream of α-methyl-γ-butyrolactone in purities ranging between 90 and 100%. A high purity of α-methyl-γ-butyrolactone minimizes problems with impurities in later steps.

In the second step of the process of the present invention, a solution of a hydrogen halide in an alkanol is added to the α-methyl-γ-butyrolactone formed in step (1) to produce a reaction mixture containing an alkyl 4-halo-2-methylbutyrate. The preparation of methyl 4-chlorobutyrate and methyl cyclopropanecarboxylate from γ-butyrolactone is disclosed in U.S. Pat. No. 3,711,549 and references cited therein. The reaction of α-methyl-γ-butyrolactone with HCl-saturated methanol for 24 hours followed by extraction into diethylether is disclosed by Ishikawa and coworkers, *Chem. Pharm. Bull.* 1995, 43, 2014. Because of its low boiling point and flammability, diethylether is not easily used on an industrial scale.

The hydrogen halide utilized in our novel process preferably is hydrogen bromide or, most preferably, hydrogen chloride. The amount of hydrogen halide used, e.g., either present in a hydrogen halide-saturated alkanol or fed to the alkanol solution of α-methyl-γ-butyrolactone, is at least 1 mole per mole of α-methyl-γ-butyrolactone, preferably about 2 to 10 moles hydrogen halide per mole of α-methyl-γ-butyrolactone. The alkanol employed may contain up to about 4 carbon atoms but preferably is methanol. The amount of alkanol used typically give an alkanol: α-methyl-γ-butyrolactone mole ratio of about 20:1 to 2:1, preferably about 10:1 to 5:1. The second step may be carried out at a temperature in the range of about 0 to 100° C., preferably about 25 to 60° C. Pressure is not important in the operation of step (2) and therefore pressures moderately above or below ambient pressure may be used. The first and second steps of our novel process normally should be carried out under anhydrous or substantially anhydrous conditions which is defined herein as less than 10 weight percent water. It is preferred that less than 5% water be present at the end of reaction.

In the third step of the process, the reaction mixture from step (2) is contacted with xylene to produce a xylene solution of an alkyl 4-halo-2-methylbutyrate. This xylene extraction of the alkyl 4-halo-2-methylbutyrate may be accomplished by intimately contacting a mixture of xylene and water with the reaction mixture from step (2). The amount of xylene typically employed in this step is about 1 to 50 parts by weight xylene per part by weight alkyl 4-halo-2-methylbutyrate present in the step (2) reaction mixture. Water may be present in the xylene-extraction mixture in amounts which give xylene:water weight ratios of about 1:0 to 1:10, preferably about 1:0 to 1:1. The extraction of step (3) may by performed at temperatures in the range of about −10 to 30° C., preferably about 0 to 25° C. Step (3) typically produces solutions comprising about 10 to 50 weight percent alkyl 4-halo-2-methylbutyrate in xylene. Any water present in the xylene solution normally is removed from the xylene solution of the alkyl 4-halo-2-methylbutyrate by azeotropic distillation to produce a substantially anhydrous xylene solution for use in step (4). Other hydrocarbons which may be used in the third step of our novel process include those with a boiling point equal to or higher than that of xylene and include naphthalene, methyinaphthalene and mesitylene. Because of its availability and favorable properties including boiling point, water azeotrope and solubility for alkyl 4-halo-2-methylbutyrate, xylene is especially preferred. The xylene may be o-, m-, or p-xylene, or ethylbenzene or may be a mixture of 2, 3 or all 4 xylene isomers.

In the fourth step of our novel process, the xylene solution of an alkyl 4-halo-2-methylbutyrate from step (3) is contacted with an alkali metal alkoxide under substantially anhydrous conditions to produce an alkyl 1-methylcyclopropanecarboxylate. We are aware of two reports of the generation of alkyl 1-methylcyclopropylcarboxylates from alkyl 4-chloro-2-methylbutyrates. Cannon et al., *J. Am. Chem. Soc.* 1959, 81, 1660, report the reaction of sodamide with ethyl 4-chloro-2-methylbutyrate under strictly anhydrous conditions in benzene to give ethyl 1-methyl-cycloproanecarboxylate in 47.6% yield. As noted above Schwarze and coworkers, U.S. Pat. No. 4,520,209, disclose the reaction of methyl 4-chloro-2-methylbutyrate in methanol with an excess of sodium methylate at a reaction temperature of 90° C. or higher and the separation of methyl 1-methylcyclopropanecarboxylate from the sodium chloride by-product using wiped film distillation or extraction.

The fourth step of the present process is performed under conditions of temperature and pressure which cause or result in the vaporization of (i) an alkanol as it is formed and (ii) an alkyl 1-methylcyclopropanecarboxylate as it is formed from the alkyl 4-halo-2-methylbutyrate. For example, the azeotropically-dried xylene solution containing methyl 4-chloro-2-methylbutyrate may be added directly to a solution of sodium methoxide in xylene and the product methyl 1-methylcyclopropanecarboxylate may be distilled directly from this reaction mixture. This technique has the advantage of retaining the co-produced sodium chloride in the undistilled xylene (bp 136–142° C.) while the product is removed (observed bp ca. 125–130° C.). The use of xylene also permits the rapid removal of methanol as it is formed from the reaction of sodium methoxide and methyl 4-chloro-2-methylbutyrate.

The alkoxide moiety of alkali metal alkoxides used in the fourth step may contain up to about 4 carbon atoms but preferably is a methoxide or ethoxide residue. The alkali metal preferably is sodium or potassium. The amount of alkali metal alkoxide used normally is at least one mole per mole of alkyl 4-chloro-2-methylbutyrate reactant. The amount of alkali metal alkoxide used preferably is about 1 to 1.3 moles of alkali metal alkoxide per mole of alkyl 4-chloro-2-methylbutyrate reactant. In a preferred mode of operation, the azeotropically-dried xylene solution containing the alkyl 4-chloro-2-methylbutyrate is added directly to a solution of the alkali metal alkoxide in xylene. Step (4) is carried out at a temperature in the range of about 100 to 200° C. to first vaporize by-product alkanol derived from the alkali metal alkoxide and then to vaporize the alkyl 1-methylcyclopropanecarboxylate as it is formed from the intermediate alkali salt of alkyl 4-halo-2-methylbutyrate. Pressure is not an important feature of step (4) and therefore pressures moderately above or below ambient pressure may be used.

The use of the preferred reactants and conditions is the basis for a preferred embodiment of the present invention for the preparation of methyl 1-methylcyclopropanecarboxylate which comprises the steps of:

(1) contacting γ-butyrolactone with dimethylcarbonate in the presence of a basic catalyst to produce α-methyl-γ-butyrolactone;

(2) contacting the α-methyl-γ-butyrolactone from step (1) with hydrogen chloride in the presence of methanol to produce a reaction mixture containing methyl 4-chloro-2-methylbutyrate;

(3) contacting the reaction mixture of step (2) with xylene to produce a substantially anhydrous xylene solution of methyl 4-chloro-2-methylbutyrate; and (4) contacting the xylene solution of methyl 4-chloro-2-methylbutyrate from step (3) with an sodium methoxide and heating at temperatures of about 100 to 200° C. which causes vaporization of (i) methanol as it is formed and (ii) methyl 1-methylcyclopropanecarboxylate as it is formed from methyl 4-chloro-2-methylbutyrate.

The alkyl 1-methylcyclopropanecarboxylate esters obtained from the process of our invention may be converted to 1-methylcyclopropylamine by the additional steps of:

(5) contacting the alkyl 1-methylcyclopropanecarboxylate produced in step (4) with an alkali metal hydroxide, carbonate or bicarbonate in the presence of water and a lower alkanol, e.g., an alkanol containing up to about 4 carbon atoms to produce an alkali metal 1-methylcyclopropanecarboxylate;

(6) contacting the alkali metal 1-methylcyclopropanecarboxylate produced in step (5) with an acid to convert the alkali metal 1-methylcyclopropanecarboxylate to 1-methylcyclopropanecarboxylic acid;

(7) contacting the 1-methylcyclopropanecarboxylic acid produced in step (6) with thionyl chloride to convert the 1-methylcyclopropanecarboxylic acid to 1-methylcyclopropanecarbonyl chloride;

(8) contacting the 1-methyl cyclopropanecarbonyl chloride from step (7) with ammonia to convert the 1-methylcyclopropanecarbonyl chloride to 1-methylcyclopropanecarboxamide; and (9) contacting the 1-methylcyclopropanecarboxamide from step (8) with an alkali metal hydroxide and an alkali metal hypochlorite in the presence of water to convert the 1-methyl cyclopropanecarboxamide to 1-methylcyclopropylamine.

As shown by the examples set forth below, two or more of steps (5)–(9) may be carried out in the same reactor without isolation of the intermediate compound. The 1-methyl cyclopropylamine produced in step (9) may be contacted with a mineral acid such as a hydrogen halide or sulfuric acid to convert the 1-methyl cyclopropylamine to its addition salt, e.g., 1-methyl cyclopropylamine hydrochloride or sulfate.

Step (5) comprises contacting the alkyl 1-methylcyclopropanecarboxylate produced in step (4) with a base selected from alkali metal hydoxide, carbonate or bicarbonate in the presence of water and a lower alkanol, e.g., an alkanol containing up to about 4 carbon atoms to produce an alkali metal 1-methyl cyclopropanecarboxylate. The base utilized in step (5) preferably is an alkali metal hydroxide, most preferably sodium or potassium hydroxide. The amount of base used normally will provide one equivalent, preferably 1 to 1.5 equivalents, of base per mole of alkyl 1-methylcyclopropanecarboxylate. The saponification of step (5) may be carried out at a temperature in the range of about 0 to 120° C., preferably about 25 to 80° C. Step (5) preferably is carried out by (i) mixing a solution of alkyl 1-methylcyclopropanecarboxylate in xylene produced in step (4) with a base selected from alkali metal hydroxide, carbonate or bicarbonate in the presence of water and a lower alkanol; (ii) heating the mixture to convert the alkyl 1-methylcyclopropanecarboxylate to an alkali metal 1-methylcyclopropanecarboxylate; (iii) allowing the reaction mixture to separate into an organic phase and an aqueous phase; and recovering the aqueous phase for step (6). Normally, the alkanol used in step (5) is removed from the aqueous phase prior to the step (6) acidification.

Step (6) comprises contacting the alkali metal 1-methylcyclopropanecarboxylate produced in step (5) with an acid in the presence of water to convert the alkali metal 1-methylcyclopropanecarboxylate to 1-methylcyclopropanecarboxylic acid. Examples of acids which may be used include the hydrogen halides such hydrochloric and hydrobromic acid and sulfuric acid. The amount of acid used usually will be about one equivalent, preferably about 1 to 1.5 equivalents, of acid per mole of alkali metal 1-methylcyclopropanecarboxylate. Step (6) may be carried out at a temperature in the range of about 0 to 100° C., preferably about 25 to 70° C. Upon completion of the reaction, the reaction mixture separates into two phases comprising an aqueous phase and an organic phase comprising the 1-methylcyclopropanecarboxylic acid product. An inert (non-reactive) hydrocarbon solvent such as toluene may be added to the reaction mixture to dilute/dissolve the 1-methylcyclopropanecarboxylic acid product followed by separation of the organic phase comprising a solution of the acid product in hydrocarbon solvent. This organic phase normally is heated to remove by distillation any water present, i.e., water dissolved in the organic phase.

In step (7) the 1-methylcyclopropanecarboxylic acid produced in step (6) is contacted with with thionyl chloride to convert the 1-methylcyclopropanecarboxylic acid to 1-methylcyclopropanecarbonyl chloride. The amount of thionyl chloride used usually will about one mole, preferably about 1 to 1.5 moles, of thionyl chloride per mole of 1-methylcyclopropanecarboxylic acid. Step (7) may be carried out at a temperature in the range of about 0 to 100° C., preferably about 50 to 90° C. This step is carried out in the presence of an inert organic solvent, preferably the hydrocarbon solvent used in step (6) to dilute/dissolve the 1-methylcyclopropanecarboxylic acid product. The reaction mixture comprising 1-methylcyclopropanecarbonyl chloride dissolved in a hydrocarbon solvent may be used in the next step without further treatment.

Step (8) comprises contacting the 1-methyl cyclopropanecarbonyl chloride from step (7) with ammonia, e.g., aqueous ammonium hydroxide, in the presence of an inert hydrocarbon solvent to convert the 1-methylcyclopropanecarbonyl chloride to 1-methylcyclopropanecarboxamide. The amount of ammonia used usually will be about one mole, preferably about 1 to 10 moles, of ammonia per mole of 1-methylcyclopropanecarbonyl chloride. Step (8) may be carried out at a temperature in the range of about −10 to 50° C., preferably about 0 to 20° C. Upon completion of the reaction and cooling of the crude reaction mixture, e.g., to 0–5° C., the amide product precipitates and may be collected by filtration.

In step (9), 1-methyl cyclopropanecarboxamide from step (8) is contacted with an alkali metal hydroxide and an alkali metal hypochlorite, e.g. sodium hypochlorite, in the presence of water to convert the 1-methylcyclopropanecarboxamide to 1-methylcyclopropylamine. The alkali metal hydroxide preferably is potassium or, most preferably, sodium hydroxide. The amount of alkali metal hydroxide employed on step (9) typically is about one mole, preferably about 2 to 6 moles, of alkali metal hydroxide per mole of 1-methylcyclopropanecarboxamide. The amount of alkali metal hypochlorite, e.g., sodium hypochlorite, used typically is about one mole, preferably about 1 to 1.5 moles, of alkali metal hypochlorite per mole of 1-methylcyclopropanecarboxamide. Step (9) may be carried out at a temperature in the range of about −5 to 100° C., preferably about 0 to 80° C. Any unreacted alkali metal hypochlorite may be decomposed by the addition of sodium thiosulfate and then the 1-methylcyclopropylamine product may be recovered as a mixture with water by simple distillation or in greater than 98% purity by fractional distillation. As mentioned above, the 1-methylcyclopropylamine may be contacted with a mineral acid such as a hydrogen halide or sulfuric acid to convert the 1-methyl cyclopropylamine to its addition salt, e.g., 1-methylcyclopropylamine hydrochloride or sulfate.

EXAMPLES

Our novel process is further illustrated by the following examples wherein all percentages given are by weight and all reactions were carried out under an inert atmosphere of argon or nitrogen, unless otherwise specified. Proton and carbon nuclear magnetic resonance (NMR) spectra were recorded on a Varian Gemini 300 NMR instrument operating at 300 MHz in proton mode and 75 MHz in carbon mode. All NMR spectra are referenced to tetramethylsilane (TMS) at 0 parts per million (ppm) and peak frequencies are recorded in ppm unless otherwise specified. NMR coupling constants (J) are reported in Hertz (Hz) as the distance between peak line frequencies and are uncorrected. Where NMR coupling constants are reported, the data were obtained at a measured resolution of less than 1.5 Hz (as measured by TMS line width at half height). Gas chromatography-mass spectroscopy (GCMS) was conducted in electron impact (ei) mode using a Hewlett Packard 5890 series II GC with a Hewlett Packard 5970 Series Mass Selective Detector controlled by Hewlett Packard Chemstation MS software. A J&W DB-5MS capillary GC column, 30 meters long, with an id of 0.25 mm and a film thickness of 0.25 micron, was used using helium carrier gas to separate the compounds for identification.

Example 1

Step (1)—Preparation of α-Methyl-γ-Butyrolactone

An autoclave having a volume 18.925 liters (5 U.S. gallons) was charged with a 5.5 weight percent solution of γ-butyrolactone in dimethylcarbonate (12.11 kg, 7.74 moles lactone) and potassium carbonate (2 kg, 14.5 moles). The autoclave was pressurized to 6.9 bara (100 psi) with nitrogen and brought to a temperature of 210° C. over a 2 hour period [initial pressure on reaching 210° C.=27.8 bara (403 psi)].

The autoclave then was heated at 210° C. with stirring for a total of 5 hours [final pressure at 210° C.=44.8 bara (650 psi)]. The autoclave then was cooled to room temperature and carefully vented. The autoclave contents were transferred to a 18.925 liters (5 U.S. gallon) carboy and filtered through a Buchner funnel (total liquids=8.9 kg; total solids after approximately 2 hours of suction drying=4.2 kg). The entire filtrate (8.9 kg) was distilled through a 15 plate Oldershaw column (29/42 fittings, approximately 30 mm inside diameter) until a base temperature of 134° C. was reached (head temperature up to 95° C.; total liquids distilled=7.2 kg of greater than 90% dimethylcarbonate by gc). The heel from this first distillation (0.934 kg) was transferred to a two-liter flask and distilled through a 15 plate Oldershaw column at 12–15 Torr up to a maximum base temperature of 153° C.). An initial forecut was taken to remove volatile materials (117 g, containing mostly dimethylcarbonate and 24% α-methyl-γ-butyrolactone by gc; bp 17–23° C., 12 Torr). A center cut was then taken (approximate ratio of α-methyl-γ-butyrolactone/γ-butyrolactone 9/1 by both gc (uncorrected FID) and NMR (molar ratio) (436 g, bp 90–98° C., 10–13 Torr, approximately 4 moles, approximately 50% yield). The heel from this distillation (301 g) contained less than 5% α-methylbutyrolactone by both gc and NMR analysis. The major component in this heel is consistent by both NMR and gcms with α-methyl-α-methoxycarbonyl-γ-butyrolactone. $^1$H NMR (CDCl$_3$) δ4.35 (m, 1H); 4.18 (m, 1H); 2.60 (m, 1H); 2.54 (m, 1H); 1.93 (m, 1H); 1.29 (d, 3H, J=7.1) GCMS (α-methyl-γ-butyrolactone): M+1=101 GCMS (α-methyl-γ-methoxycarbonyl-γ-butyrolactone): M+1=159

Step (2)—Preparation of Methyl 4-Chloro-2-Methylbutyrate

α-Methyl-γ-butyrolactone (7 kg, 69.9 moles) and methanol (20 L) were added to a water cooled 50 L glass reactor equipped for mechanical stirring and equipped with a water cooled reflux condenser. Anhydrous HCl was introduced through a gas inlet tube (approximately 2.5 cm−1 inch subsurface, approximately 10 mm inside diameter) at an inlet tube pressure of approximately 1.15 bara (16.7 psi). HCl addition was terminated after 6–12 hours or when the reaction temperature exceeded approximately 50° C. The off-gasses were passed through a water scrubber. The progress of the reaction was monitored by gc and was at greater than 80% conversion after 24–36 hours.

Step (3)—Preparation of Xylene Solution of Methyl 4-Chloro-2-Methylbutyrate

A second 50 L reactor (equipped for mechanical stirring) was charged with ice (5 kg), water (10 kg) and mixed xylenes (3 L). Approximately ⅓ of the HCl-containing crude reaction mixture from step (2) above was added to this stirred suspension of water and xylene. After brief stirring (approximately 2 minutes) the phases were allowed to separate (approximately 5 minutes) and the organic phase was isolated. These extractions were then repeated for the remaining ⅔ of the HCl-containing crude reaction mixture. The gc-determined concentration of methyl 4-chloro-2-methylbutyrate was approximately 44 weight percent. The xylene extracts from three 50 L methanol/HCl reactions were combined and the solution was dried by distillation of approximately 2 L of xylene-water azeotrope. This material was used directly as the feed for step (4). NMR determined concentration of methyl 4-chloro-2-methylbutyrate: 51 weight %, 45.1 kg, 153 moles, 73% yield). $^1$H NMR (CDCl$_3$) δ3.70 (s, 3H); 3.57 (apparentt, 2H, J=6.6); 2.73 (m, 1H); 2.23 (m, 1H); 2.2 (m, 1H); 1.86 (m, 1H); 1.20 (d, 3H, J=6.4) GCMS: M+1=151, 153

Step (4)—Preparation of Methyl 1-Methylcyclopropanecarboxylate

Mixed xylenes (51.7 kg) were charged to a nitrogen-purged, 100-L, glass-lined reactor. This reactor is equipped with a 15.2 cm (6 inch) diameter glass distillation column packed with 54 inches of 6.35 mm (0.25 inch) HC-276 Penn State packing. A portion of the xylenes (8.8 kg) were distilled off to insure that the remaining solution was anhydrous. The reactor was cooled to less than 80° C. and a 25 weight percent solution of methanolic sodium methoxide (39.5 kg, 183 moles) was added. Distillate was removed up to a column head temperature of 120° C. to insure that the reactor was methanol free. The reactor was again cooled to under 80° C. and was then charged with the methyl 4-chloro-2-methylbutyrate (45.1 kg, 51 weight percent in xylenes as estimated by NMR, 153 moles) obtained in step (4). Distillate then was rapidly collected at a reflux ratio of less than 6/1 until the head temperature reached 125° C. Heat input to the reactor was then set to 160° C. The reflux ratio then was slowly adjusted up to 29/1 in order to keep the column head temperature between 125° C. and 130° C. With heat input to the reactor at 160° C. and the reflux ratio at 29/1 the column head temperature was allowed to rise to approximately 136° C. until gc analysis of the distillate indicated a declining concentration of methyl 1-methylcyclopropanecarboxylate (less than 5 weight percent). A typical reactor cycle time (from start through cleanout) was approximately 40 hours. The total amount of methyl 1-methylcyclopropanecarboxylate (approximately 17.2 kg, dry weight basis) collected represented a yield of approximately 91%. Typical concentrations of methyl 1-methylcyclopropanecarboxylate in mixed xylenes were in excess of 50%. The initial 3.3 kg of distillate collected in this step (4) contained less than 0.2 weight percent of methyl 1-methylcyclopropanecarboxylate, more than 5% xylenes and greater than 90 weight percent of methanol as determined by gc. The next 3.6 kg of distillate contained approximately 30 weight percent of methyl 1-methylcyclopropanecarboxylate. The following 3.7 kg of distillate contained approximately 58 weight percent of methyl 1-methylcyclopropanecarboxylate. $^1$H NMR (CDCl$_3$) δ3.65 (s, 3H); 1.29 (s, 3H); 1.22 (m, 2H); 0.66 (m, 2H) GCMS: M+1=115

The methyl 1-methylcyclopropanecarboxylate may be converted to 1-methylcyclopropylamine according to the following procedures:

Preparation of 1-Methylcyclopropanecarboxylic Acid

The solution (318.3 g) of approximately 55.2% methyl 1-methylcyclopropanecarboxylate (176 g, 1.54 moles) in xylene prepared as in step (4) above was combined with 89 mL of methanol and 89 mL of water in a 1-L, 3-necked flask equipped with an addition funnel and a mechanical stirrer. The reaction mixture was heated to and held at 50–55° C. 50% Aqueous sodium hydroxide (85 mL; 1.60 moles; 1.1 equiv.) was added to the flask over 50 minutes at a rate such that the temperature of the reaction was maintained below 62° C. After the addition was complete the reaction mixture was heated at 60±2° C. for 2 hours to completely consume the methyl 1-methyl-cyclopropanecarboxylate. The mixture was cooled to ambient temperature and allowed to settle for 5 minutes. The lower aqueous layer was decanted and saved. The upper organic layer (125.75 g; about 140 mL) was discarded. The aqueous solution was returned to the flask and the methanol contained therein was removed by distillation at atmospheric pressure with full takeoff to a column head temperature of 86° C. A total of 140 mL (118.2 g) of distillate was collected. The flask was allowed to cool to ambient temperature and water (75 mL) was added. Concentrated (36%) HCl (167 mL; 2.00 moles; 1.3 equiv.) was added at a rate and with cooling such that the temperature remained below 50° C. The resulting mixture consisted of two layers with precipitated salts in the bottom layer. Water (25 mL) was added to dissolve the salts, toluene (100 mL) was added, and the resulting solution was thoroughly mixed and allowed to separate. The lower aqueous layer (441.7 g; ca. 370 mL) was decanted and discarded. The upper layer was diluted with 120 mL of toluene and distilled at atmospheric pressure to remove water. The distillation was carried to a column head temperature of 111° C. (required 72 mL) after which point a further 73 mL was distilled. The flask then was cooled and drained to afford 216.5 g of a solution containing 71.1% 1-methylcyclopropanecarboxylic acid in toluene (as determined by NMR; about 153.9 g, 1.54 mol, approximately 100%). $^1$H NMR (CDCl$_3$) δ1.28 (m, 5H); 0.75 (m, 2H)

Preparation of 1-Methylcyclopropanecarboxamide

A 77.7 weight percent solution of 1-methylcyclopropanecarboxylic acid in toluene (185.66 g of solution; about 144.24 g; 1.44 moles) prepared as described above and toluene (42 mL) were added to a 1-L, 4-necked flask equipped with a magnetic stirrer, an addition funnel, and a nitrogen T inlet linked to a water scrubber. The solution was heated to 45° C. and thionyl chloride (116 mL; 1.58 moles; 1.1 equiv.) was added over 1 hour. The addition was accompanied by gas evolution and a mild endotherm. After the addition was complete the reaction mixture was heated to 80° C. for 5 hours at which point no 1-methylcyclopropanecarboxylic acid was present according to GC analysis.

Ammonium hydroxide (28% NH$_3$; 390 mL; 5.76 moles; 4 equiv.) was added to a 2-L, 3-necked flask equipped with a mechanical stirrer and an addition funnel. The contents of the thionyl chloride reaction were placed into the addition funnel and washed in with a little toluene. The ammonium hydroxide was cooled in an ice-acetone bath and the contents of the addition funnel were added over 1 hour such that the reaction mixture was maintained below 25° C. Once the addition was complete the mixture was cooled to 0–5° C. in an ice-water bath for 1 hour. The precipitated 1-methylcycpropanecarboxamide was collected by filtration, washed with ice-cold water, and air-dried to afford 119.4 g (84%) of 1-methylcycpropanecarboxamide as a white solid, mp 144–145° C. $^1$H NMR (DMSO) δ7.03 (bs, 1H); 6.83 (bs, 1H); 1.19 (s, 3H); 0.89 (m, 2H); 0.45 (m, 2H)

Preparation of 1-Methylcyclopropylamine Hydrochloride

Water (190 mL) and 50% sodium hydroxide (104.9 mL; 160 g; 2.0 mol) were combined and cooled to below 5° C. 1-Methylcyclopropanecarboxamide (60.4 g; 82% solids; 49.6 g 100% basis; 0.5 mol) was added and washed in with 60 mL water. The reaction was placed in an ice-acetone bath and the addition of aqueous sodium hypochlorite (12.68% aqueous solution; 268 mL; 0.55 mol; 1.1 equiv) was begun. The addition was carried out over 30 minutes such that the temperature was maintained between 0 and 5° C. The mixture was stirred at 0–5° C. for 1 hour. The reaction mixture was allowed to warm to ambient temperature and stir for 2 hours at which point all solids had dissolved. GC analysis of an aliquot indicated no caboxamide reactant present. One mL of 2 M sodium thiosulfate was added to destroy any excess oxidant and the reaction mixture was heated to 60° C. for 2 hours to decompose the carbamate intermediate. A distillation head was fitted to the flask and material boiling from ambient temperature up to a head temperature of 91° C. (43.78 g) was collected. The distillate contained an approximate 84:16 weight:weight mixture of 1-methylcyclopropylamine and water, respectively. The distillate was dissolved in 173 mL of n-butanol and cooled in an ice-water bath. Concentrated hydrochloric acid was added such that the temperature remained below 20° C. A Dean-Stark trap was placed on the flask and the mixture heated. A total of 39 mL of water were removed (head temperature at end of water removal was 111.5° C.). The trap was drained and an additional 77 mL of butanol distilled (final pot temperature was 125° C.). The heating mantle was removed from the flask and heptane (228 mL) was slowly added to the hot solution. Product crystallized at 109° C. The temperature at end of the heptane addition was 70° C. The resulting slurry was allowed to cool to ambient temperature and then cooled to 0–5° C. for 1 hour. The resulting glistening white solid was collected, washed with heptane (3×50 mL) and air-dried to afford 41.45 g (77%) of 1-methylcyclopropaneamine hydrochloride, mp 203–204° C. $^1$H NMR (DMSO) $\delta$8.35(bs, 3H); 1.38(s, 3H); 0.9 (t, 2H); 0.62(t, 2H).

The invention has been described in detail with particular reference to preferred embodiments thereof, but it will be understood that variations and modifications can be effected within the spirit and scope of the invention.

We claim:

1. Process for the preparation of alkyl 1-methylcyclopropanecarboxylate which comprises the steps of:
   (1) contacting γ-butyrolactone with dimethylcarbonate in the presence of a basic catalyst to produce α-methyl-γ-butyrolactone;
   (2) contacting the α-methyl-γ-butyrolactone from step (1) with a hydrogen halide in the presence of an alkanol, wherein said alkanol is methanol or ethanol, to produce a reaction mixture containing an alkyl 4-halo-2-methylbutyrate;
   (3) contacting the reaction mixture of step (2) with xylene to produce a xylene solution of an alkyl 4-halo-2-methylbutyrate;
   (4) contacting the xylene solution of an alkyl 4-halo-2-methylbutyrate from step (3) with an alkali metal alkoxide under conditions of temperature and pressure which causes vaporization of (i) an alkanol as it is formed and (ii) an alkyl 1-methylcyclopropanecarboxylate as it is formed from the alkyl 4-halo-2-methylbutyrate.

2. Process according to claim 1 wherein step (1) is carried out at a temperature of about 200 to 240° C. at a pressure of about 27 to 90 bars absolute and the basic catalyst is selected from the alkali metal hydroxides, carbonates and bicarbonates; step (2) is carried out using 2 to 10 moles of hydrogen chloride per mole of α-methyl-γ-butyrolactone; step (3) is carried out using 1 to 5 parts by weight xylene per part by weight alkyl 4-halo-2-methylbutyrate and a temperature of about 0 to 25° C.; and step (4) is carried out using an alkali metal alkoxide containing up to about 4 carbon atoms and a temperature of about 100 to 200° C.

3. Process according to claim 2 wherein step (1) is carried out at a temperature of about 210 to 240° C. and using potassium carbonate as the basic catalyst; step (2) is carried out using 2 to 10 moles of hydrogen chloride per mole of α-methyl-γ-butyrolactone, methanol as the alkanol, and a temperature of about 25 to 60° C.; and step (4) is carried out using 1 to 1.3 moles of sodium or potassium methoxide or ethoxide per mole alkyl 4-halo-2-methylbutyrate.

4. Process for the preparation of methyl 1-methylcyclopropanecarboxylate which comprises the steps of:
   (1) contacting γ-butyrolactone with dimethylcarbonate in the presence of a basic catalyst to produce α-methyl-γ-butyrolactone;
   (2) contacting the α-methyl-γ-butyrolactone from step (1) with a hydrogen chloride in the presence of an methanol to produce a reaction mixture containing methyl 4-chloro-2-methylbutyrate;
   (3) contacting the reaction mixture of step (2) with xylene to produce a substantially anhydrous xylene solution of methyl 4-chloro-2-methylbutyrate;
   (4) contacting the xylene solution of methyl 4-chloro-2-methylbutyrate from step (3) with an sodium methoxide and heating at temperatures of about 100 to 200° C. which causes vaporization of (i) methanol as it is formed and (ii) methyl 1-methylcyclopropanecarboxylate as it is formed from methyl 4-chloro-2-methylbutyrate.

5. Process according to claim 4 wherein step (1) is carried out at a temperature of about 210 to 240° C. and at a pressure of about 27 to 90 bars absolute and the basic catalyst is potassium carbonate; step (2) is carried out using 2 to 10 moles of hydrogen chloride per mole of α-methyl-γ-butyrolactone and methanol as the alkanol; step (3) is carried out using 1 to 5 parts by weight xylene per part by weight alkyl 4-halo-2-methylbutyrate and a temperature of about 0 to 25° C.; and step (4) is carried out using 1 to 1.3 moles of sodium or potassium methoxide or ethoxide per mole of alkyl 4-halo-2-methylbutyrate and a temperature of about 100 to 200° C.

6. Process according to claim 1 which includes the steps of:
   (5) contacting the alkyl 1-methylcyclopropanecarboxylate produced in step (4) with an alkali metal hydroxide, carbonate or bicarbonate in the presence of water and a lower alkanol, e.g., an alkanol containing up to about 4 carbon atoms to produce an alkali metal 1-methylcyclopropanecarboxylate;
   (6) contacting the alkali metal 1-methylcyclopropanecarboxylate produced in step (5) with an acid to convert the alkali metal 1-methylcyclopropanecarboxylate to 1-methylcyclopropanecarboxylic acid;
   (7) contacting the 1-methylcyclopropanecarboxylic acid produced in step (6) with thionyl chloride to convert the 1-methylcyclopropanecarboxylic acid to 1-methylcyclopropanecarbonyl chloride;
   (8) contacting the 1-methyl cyclopropanecarbonyl chloride from step (7) with ammonia to convert the 1-methyl cyclopropanecarbonyl chloride to 1-methyl cyclopropanecarboxamide; and
   (9) contacting the 1-methyl cyclopropanecarboxamide from step (8) with an alkali metal hydroxide and an alkali metal hypochlorite in the presence of water to convert the 1-methyl cyclopropanecarboxamide to 1-methyl cyclopropylamine.

7. Process for the preparation and recovery of an alkyl 1-methylcyclopropanecarboxylate which comprises contacting a xylene solution of an alkyl 4-halo-2-methylbutyrate with an alkali metal alkoxide under conditions of temperature and pressure which causes vaporization of (i) an alkanol as it is formed and (ii) an alkyl 1-methylcyclopropanecarboxylate as it is formed from the alkyl 4-halo-2-methylbutyrate.

8. Process according to claim 7 for the preparation of methyl 1-methylcyclopropanecarboxylate which comprises contacting a xylene solution of a methyl 4-chloro-2-methylbutyrate with sodium methoxide and heating at temperatures in the range of 100 to 200° C. which causes vaporization of (i) methanol as it is formed and (ii) methyl 1-methylcyclopropanecarboxylate as it is formed.

9. A process according to claim 1 wherein the α-methyl-γ-butyrolactone produced in step (1) is purified by distillation to a purity of greater than 90%.

10. A process according to claim 4 wherein the α-methyl-γ-butyrolactone produced in step (1) is purified by distillation to a purity of greater than 90%.

* * * * *